United States Patent [19]

Becker et al.

[11] Patent Number: 5,731,164
[45] Date of Patent: Mar. 24, 1998

[54] METHOD OF CHECKING THE RATE OF REMOVAL OF PYROGENIC SUBSTANCES, IN PARTICULAR VIRUSES, FROM ORGANIC MATERIAL

[75] Inventors: Gerhard Becker, Bühl Baden; Paul Marcel Larson, Malsch; Reiner Heidl, Asslar-Werdorf, all of Germany

[73] Assignee: Sanorell Pharma GmbH & Co., Baiersbronn, Germany

[21] Appl. No.: 458,022

[22] Filed: Jun. 1, 1995

Related U.S. Application Data

[63] Continuation of Ser. No. 190,167, filed as PCT/DE92/00653, Aug. 5, 1992, published as WO94/02782, Feb. 3, 1994, abandoned.

[30] Foreign Application Priority Data

Aug. 6, 1991 [DE] Germany ............... 41 26 034.1

[51] Int. Cl.$^6$ ............... C12Q 1/22; G01N 7/00; C02E 1/44
[52] U.S. Cl. ............... 435/31; 435/29; 435/34; 435/39; 435/261; 436/146; 436/148; 436/175; 436/825; 210/637; 210/650; 210/651; 422/82.13; 422/88
[58] Field of Search ............... 435/31, 29, 34, 435/39, 26; 436/146, 148, 175, 825; 210/637, 650, 651; 422/82.13, 88

[56] References Cited

U.S. PATENT DOCUMENTS

| | | | |
|---|---|---|---|
| 4,610,790 | 9/1986 | Reti et al. | 210/636 |
| 4,808,315 | 2/1989 | Manabe et al. | 210/645 |
| 4,865,726 | 9/1989 | De Vries | 210/137 |
| 4,883,596 | 11/1989 | Agui et al | 210/638 |
| 4,909,942 | 3/1990 | Sato et al. | 210/651 |
| 5,104,546 | 4/1992 | Filson et al. | 210/650 |
| 5,116,736 | 5/1992 | Tahara et al. | 435/39 |
| 5,221,483 | 6/1993 | Glenn et al. | 210/641 |

*Primary Examiner*—Cecilia J. Tsang
*Assistant Examiner*—Abdel A. Mohamed
*Attorney, Agent, or Firm*—John P. White

[57] ABSTRACT

This invention provides a process for checking the removal rate of pyrogenic substances, in particular viruses, from organic material. The material to be purified is passed through an ultrafilter or an ultrafiltration unit whose virus-removal rate has already been determined by passing viruses of the Leviviridae family or other comparable small bacteriophages through the filter or filtration unit, the virus titer is determined before and after the filtration operation and the virus removal rate thus calculated. Before or after determining the virus-removal rate, a given pressure is applied to the filter or filtration unit in a gas pressure-hold test, and the decrease in the pressure over a given period is measured. After filtration of the biological material, the rate of virus removal by the filter is checked by repeating the pressure-hold test.

20 Claims, No Drawings

METHOD OF CHECKING THE RATE OF REMOVAL OF PYROGENIC SUBSTANCES, IN PARTICULAR VIRUSES, FROM ORGANIC MATERIAL

This application is a continuation of U.S. Ser. No. 08/190,167, filed Apr. 7, 1994, now abandoned corresponding to PCT International Application No. PCT/DE92/00653, filed Aug. 5, 1992, published as WO94/02782, Feb. 3, 1994, claiming priority of German Application No. P41 26 034.1, filed Aug. 6, 1991.

The invention relates to a method of checking the rate of removal of pyrogenic substances, in particular viruses, from organic material, whereby the material to be purified is passed through an ultrafilter or ultrafiltration unit, whose rate of removal was determined by passing viruses of the family Leviviridae or other comparable small bacteriophages through the filter or filtration unit, and determining the titer of the viruses before and after filtration, from which the rate of removal was calculated.

Drugs obtained from cell cultures, organs, or blood of animals or humans are potentially contaminated with viruses pathogenic to animals or humans or with other pyrogenic material. In consideration of the broad range of viruses with which a specimen may be contaminated, it is impossible to test the starting material for all viruses which could be present. Moreover, reliable or sufficiently sensitive detection methods are lacking for some virus groups. Consequently, a purification or inactivation process must be conducted, whereby pathogenic viruses are removed, so that no problems are to be expected, even in case of a massive infection of the starting material or intermediate products. The purification or inactivation process should be so efficient that viruses can be removed at rates of up to $10^{12}$.

Sterile filtration has been applied to eliminate bacteria in the preparation of drugs for a long time. It is considered to be a reliable decontamination process for these potential pathogens. The sterile filters are thereby passed by random sampling by the manufacturer with the bacterium *Pseudomanas diminuta*, the smallest known bacterium, outside the Mycoplasma and L-form groups. If it is possible to detect a certain removal rate in sterile filtration for this bacterium in the bacteria challenge test, the production lot is considered safe. Such a process is described in Wallh äuser, *Praxis der Sterilisation*, Thieme pub., Stuttgart, 1988, pp. 324 ff.

A filtration process can also be applied for the removal of viruses, where the filters used must retain molecules and particles of over 1 million daltons. Such ultrafilters are available in the most varied designs but, in contrast to sterile filters, no absolute filters are involved, i.e., molecules and particles of over 1 million daltons are not absolutely retained, but only to a large extent. The retention rate is thereby not only dependent on the filter type, but it may even vary from production lot to production lot. Ultrafilters therefore have not hitherto been introduced for virus removal, but instead perhaps contributed to total virus removal in a production process consisting of several steps (Werner and Langlius-Gane, Meeting the Regulatory Requirements for Pharmaceutical Production of Recombinant and Derived Products, Arzneimittel-Forschung 39:108–111, 1989). This unreliability of ultrafilters is based on the filter production process. In ultrafilters provided for a definite molecular weight exclusion, it is always possible for larger micropores to appear, which may be passable for viruses, for example. Moreover, unlike, microfilters, ultrafilters cannot be tested for tightness by the so-called bubble-point process.

In the unpublished DE-A-40 03 543.3 and PCT/DE 91/00099, whose content is herewith expressly made the object of the specification, a process is described for determining the removal rate of viruses, which also provides information concerning which filtration process provides a removal considered reliable, and through how many filtration steps. The removal rate is determined by passing viruses of the family Leviviridae through the filter or filtration unit, determining the titer of the viruses before and after filtration, and calculating the removal rate from this.

It is also possible to use other comparable small bacteriophages. These bacteriophages are preferably detectable by simple holes in a bacterial growth area.

However, this process presents the disadvantage that, after the use of a filter calibrated in this way, the removal rate must again be determined by the process described above, in order to make sure that no injury to the filter, for example the appearance of holes, fissures, etc., has developed before or during filtration, such as to prevent retention of the pyrogenic material to be removed. However, this additional determination of the removal rate requires an outlay in time and material, which increases production and personnel costs, as well as apparatus outlays, if viruses in solutions are to be removed on an industrial scale by this process.

A rapid simple process, capable of being executed without too great cost, with which the once-calculated removal rate of the filter can be checked, is therefore required.

This object is attained according to the invention by a process for checking the removal rate of pyrogenic substances, especially viruses in organic material, characterized by the fact that material to be purified is passed through an ultrafilter or ultrafiltration unit whose removal rate was previously calculated, by passing viruses of the family Leviviridae or other comparable small bacteriophages through the filter or filtration unit, calculating the virus titers before and after filtration, and from this the removal rate and, before or after determining the removal rate, applying a predetermined test pressure in a gas pressure-hold test to the filter or filtration unit-and, after filtration of the biological material, checking the removal rate of the filter by again making the pressure-hold test.

It was found, according to the invention, that the removal rate of a filter or filtration unit is constant as long as the pressure fall in a pressure-hold test (a so-called forward-flow test) is also constant. If the behavior of the filter changes in such a test, a change in the structure of the micropores or a microscopic distortion of the filter structure exists, which prevents retention of the pyrogenic substance to be removed and permits it to pass unhindered through the filter. The removal rate of the filter is thereby worsened. The procedure adopted on the basis of experience is that of subjecting a filter whose removal rate is to be determined, with its side turned to the material to be filtered, to a gas of a predetermined pressure, and determining the fall in pressure per unit of time after a stabilization period. The stabilization time is to be selected so that the pressure appearing becomes stabilized over all parts appearing in the system. The amount of the predetermined pressure to be applied can easily be determined by the expert through simple experiments, depending on the filter used and the gas in the given case. However, it should be below the destruction pressure of the filter, in order not to destroy the integrity of the membrane by the test. The maximum permissible pressure fall can be determined directly by the expert through simple experiments, depending on the filter used in the given case. After the characteristic pressure fall for the removal rate for a given filter has been determined in this way, following filtration of the biological material, the removal rate of the filter can be checked by determining only the pressure fall by means of a further pressure-hold test and comparing this with the previously determined characteristic pressure fall for the given removal rate. If no deviations or only slight changes in pressure fall appear, it can be assumed, on the basis of experience, that the removal rate of the filter has not been altered by use. It is therefore possible, with the process according to the invention, to check the quality of a validated filter in a simple and easily executed way after each use, without incurring a great expense.

In a preferred form of execution, the pressure-hold test is conducted on a filter which has been moistened. Preferred moistening agents are water, or aqueous solutions, and mixtures of water and an organic solvent. Preferred aqueous solutions include aqueous basic solutions, especially dilute solutions of NaOH, KOH, and $NH_3$. According to the organic material to be used, dilute solutions of weak mineral or organic acids may also be used as wetting agents. Preferred organic solvents particularly include alcohols and ketones, where methanol, ethanol, propanol, and isopropanol are particularly preferred. If the filters are to be moistened with the above mentioned aqueous solutions, care is to be taken to use only solutions which are compatible with the filter material.

In another preferred form of execution according to the invention, a certain time is allowed to elapse after applying the pressure test, until the pressure fall in the system to be measured has stabilized. The stabilization duration depends on the test system to be measured in a given case. It can directly be determined by an expert through simple experiments. In the case of commercial filters, the usual stabilization times are 30 to 600 seconds, especially 200 to 400 seconds.

The test time in which the pressure fall is determined also depends on the system to be tested and the desired precision. It can also easily be determined directly by an expert. The usual test times are 15 to 900 seconds, preferably between 200 and 600 seconds. Test times of 250 to 300 seconds are suitably selected.

It was found suitable to conduct the check of the removal after filtration has taken place under precisely the same conditions as before the filtration. However, it is also possible, according to the invention, to conduct the check test under other conditions if advisable, and if it has been determined that the pressure fall thereby measured can be assigned to a removal rate.

In the process according to the invention, it was found suitable to use air and/or inert gases as the gas for the pressure-hold test. Nitrogen, oxygen, and hydrogen are preferred, and helium is preferred from among the inert gases. Hydrogen or helium were found preferable for measurements to be made especially rapidly, or in the case of membranes with particularly small pores.

With the method according to the invention, it is possible to conduct an ultrafiltration as the only method for an assured virus removal, without additional purification or inactivation steps, by checking the removal rate of the pyrogenic substances in the running process. If this removal rate is determined before and after filtration of the production load, and it is higher than $10^{12}$, it is possible to exclude a virus contamination of the product with quite high certainty. Validation experiments have hitherto been conducted only with animal or even with human pathogenic viruses. Consequently, for safety reasons, the validated filters could no longer be used after that. For this reason, it was then necessary to introduce new filters with possibly different removal rates. Such a validation was therefore valid for only a single filter, and moreover, it could be made only once before or after a removal as an example, because of the cost entailed by it. On the other hand, it is possible, according to the invention, to check the removal of pyrogenic or pathogenic substances, viruses, for example, in one process.

According to the process, the solution to be purified, or the gas to be purified, is passed through a filter or filtration unit whose removal rate had previously been determined. By introducing viruses of the group Leviviridae as test virus, the removal rate is reliably determined. By a prior or subsequent pressure-hold test, the removal rate thus determined is assigned a decrease in pressure at predetermined conditions; as long as the decrease in pressure is found comparable in later check measurements, it can be assumed that the removal rate has remained the same.

The Leviviridae used for determining the removal rate, 23 nm in diameter and with a molecular weight of 1.4 million daltons, are smaller than viruses pathogenic to humans and animals (H. Fraenkel-Conrat, The Viruses, Catalogue, Characterization and Classification, Plenum Press, 1982). They attack only certain $F^+$ strains of the harmless intestinal bacterium *Escherichia coli* and, as RNA viruses, are already hydrolyzed in 10-mM NaOH in a short time, thereby being decomposed into their individual molecular components. The smallest animal and/or human pathogenic viruses come from the group of Picornaviruses; they are 27 nm in diameter and are 2.5 million daltons in weight. Leviviridae are therefore suitable for validation of ultrafilters to be selected for size. The filters can be washed with 0.1-N NaOH after that, whereby pyrogens coming from *Escherichia coli* are also removed. The filters are then again ready for use for production. The conditions defined for in process control ate thereby satisfied, namely by:

a simple and exact validation process, capable of execution in a short time;

the filters tested can be reused without additional contamination of the product.

In addition, the Leviviridae can be applied at extremely high titers of up to $10^{14}$ pfu per ml and can reliably be detected at even concentrations of 1 pfu per ml by a simple plate process.

For a determination, a virus solution with a titer of more than $10^{10}$ pfu/ml is passed through the filter, and the concentration of phages in the filtrate and retained solution is determined. The determination is made in a known way (for example, after the top agar method of N. H. Adams (1959), Bacteriophages, Interscience Publishers, New York). For the purpose, for example, the phages are mixed with suitable host bacteria (e.g., *E. coli* 3300, ATCC No. 19853) and are applied in a layer of 0.6% agar on plates with nutrient agar (e.g., 1% bactotrypton, 0.5% yeast extract, 0.5% NaCl, 0.1 mM $CaCl_2$, 1.5% agar) $10^7$ to $10^8$ bacteria and less than 100 phages should be applied per plate. The plates are then incubated at 37° C., whereupon a bacterial growth develops after 10 hours. Holes in this growth reveal virus attack. The number of holes presents the virus titer in pfu (plaque-forming units). Since one virus can cause a plaque, even 1 virus per ml can be detected with standard agar plates. A virus concentration of more than $10^{14}$ to 1 pfu per ml can thus be covered.

The virus removal rate is then obtained by determining the virus concentrations in the filtrate and in the solution before filtration. By determining the virus titer in the concentrate (i.e., the solution retained before the filter), it is possible to calculate whether viruses are lost by absorption at the filter or inactivation, which gives the validation process an additional reliability.

Since the removal rate of filtration membranes can vary considerably not only from manufacturer to manufacturer, but also from production lot to production lot, it is essential to determine the removal rate for pyrogenic substances for each individual filter.

It is preferable to test the filter or filter unit provided for purifying organic material under precisely defined pressure conditions, which can then also be maintained later in the removal process.

After determining the removal rate of bacteriophages and other residues such as pyrogens, the filters can then be used for the purification process of organic material after simply rinsing with sodium hydroxide solution. This is another advantage of the process according to the invention, since this would not be possible with the use of viruses pathogenic to animals or humans, because of the great danger of contamination with such viruses.

The invention is illustrated in detail below by examples.

EXAMPLE 1

Removal of Test Viruses by Factor 12

Filtration cartridge S1Y30 with serial number 10330 was tested. The phage solution consisted of 600 ml phage buffer (methods) with 600 mg bovine serum albumin and 50 ml phage concentrate (titer: $1.3 \times 10^{12}$ pfu (plaque forming units)/ml. The filtration was first done three consecutive times. The volume of the filtrate decreased from 600 to 400 to 380 ml. The filtration times for each step were about 20 minutes. The cartridge was washed with 1 liter 10-mM sodium hydroxide between each filtration to inactivate phage residues, and was then rinsed to neutrality with distilled water (measured with the pH electrode).

The virus contents in the individual filtrates were determined. They are presented in Table 1.

It appears from the virus removal rate data (Table 1), that with the use of the ultrafiltration cartridge the virus titer decreased by 6.92 and 7.22 common logarithms after the first filtration. After the second filtration in the given case, already no further phages were detectable in the filtrate. The viruses after the first two filtrations were accordingly reduced by a total of 11 powers of ten, and were reduced by 11.7 powers of ten after the further two filtrations, from which a total reduction of 22.7 powers of ten after four filtrations can be calculated. The removal of by 12 to 16 powers of ten frequently recommended in the literature was already exceeded after three filtrations, with 18.22 powers of ten.

EXAMPLE 2

Testing the Removal Ability of Test Viruses by Means of the Pressure Decrease Characteristic of an Ultrafilter The filter validated in Example 1 is subjected to a non-destructive pressure-hold test in a Palltronic FFE-03 integration test unit (obtainable from Pall Filtrationstechnik GmbH at D-6072 Dreieich 1). The rinsed and washed ultrafiltration cartridge was thereby subjected to several consecutive pressure-hold tests (forward flow tests), which were conducted as follows:

The filtration cartridge was introduced into the test unit at 1 bar nitrogen pressure. After a stabilization time of 300 seconds, the decrease in pressure was measured over a period of 300 seconds. A decrease in pressure of 5 mbar, 13 mbar, and 10 mbar was thereby measured in all cases. After the measurement ended, the cartridge was automatically ventilated and the measurement result printed out.

EXAMPLE 3

A thymus extract was filtered with the filtration cartridge of Example 2.

Extract obtained from the thymus gland in a known way was filtered, and the decrease in BSA was checked by means of an HPLC in inverse phase. The filtration cartridge was purified after that, and the decrease in pressure was determined by the pressure-hold test, as described in Example 2. Pressure decreases of 5 and 14 mbar were thereby determined. This indicated that the virus removal rate had not changed.

Bacteriophage fr (ATCC 15767-B1) was filed on Nov. 19, 1964 with the American Type Culture Collection, 12301 Parklawn Drive, Rockville, Md. 20852-1776 USA. It has been freely available since Nov. 19, 1964.

E. coli 3300 (ATCC 19853) was filed on Jan. 12, 1967 with the American Type Culture Collection, 12301 Parklawn Drive, Rockville, Md. 20852-1776 USA. It has been freely available since Jan. 12, 1967.

TABLE 1

Virus titers in the filtrates of the individual filtration steps with the Amicon S1Y30 ultrafiltration cartridge

| Filtration step | Virus titer (pfu/ml) |
| --- | --- |
| Starting material | $1 \times 10^{11}$ |
| First filtration | $1.2 \times 10^4$ |
| Second filtration | 0 |
| Third filtration | 0 |
| Addition of new test phages | $5 \times 10^{11}$ |
| First filtration | $3 \times 10^4$ |
| Second filtration | 0 |
| Third filtration | 0 |

We claim:

1. A process for validating the integrity of an ultrafilter or ultrafiltration unit for removing pyrogenic substances in organic material, comprising:

(a) calibrating the removal rate of an ultrafilter or an ultrafiltration unit by introducing viruses of the Leviviridae family or another bacteriophage having a diameter of less than 27 nanometers into the ultrafilter or the ultrafiltration unit;

(b) determining a first virus titer before ultrafiltration and a second virus titer after ultrafiltration;

(c) calculating the removal rate from (b);

(d) applying a gas at a predetermined pressure to the ultrafilter or the ultrafiltration unit in a first pressure-hold test either before or after calculating the removal rate;

(e) determining the decrease in pressure over a predetermined time;

(f) passing the organic material to be purified over the ultrafilter or the ultrafiltration unit whose removal rate was previously determined by steps (a)–(c);

(g) applying the gas used in step (d) at the same predetermined pressure to the ultrafilter or the ultrafiltration unit in a second pressure-hold test to determine a decrease in pressure, over a predetermined time; a comparable decrease in pressure indicating that the removal rate of the ultrafilter or ultrafiltration unit has not changed; thereby validating the integrity of the ultrafilter or the ultrafiltration unit.

2. The process of claim 1, wherein the decrease in pressure determined in step (g) is determined at an ultrafilter which is moistened with a substance selected from the group consisting of water, an aqueous solution, and a mixture of water and an organic solvent.

3. The process of claim 2, wherein an aqueous solution is selected from a group consisting of dilute NaOH, dilute KOH and dilute $NH_3$ solution.

4. The process of claims 1, 2 or 3, wherein the decrease in pressure is determined only after a stabilization time.

5. The process of claims 1, 2 or 3, wherein the measurement of the decrease in pressure is done after ultrafiltration under the same conditions as before the ultrafiltration.

6. The process of claims 1, 2 or 3, wherein the gas used is selected from a group consisting of air, nitrogen, oxygen, hydrogen, and helium.

7. The process of claim 1, wherein the pyrogenic substance is a pathogen.

8. The process of claim 7, wherein the pathogen is a virus.

9. The process of claim 1, further comprising eliminating any pyrogens retained on the ultrafilter or ultrafiltration unit after step (g) by passing a solution capable of dissolving the pyrogens on the ultrafilter or ultrafiltration unit.

10. The process of claim 9, wherein the solution capable of dissolving the pyrogens is an alkaline solution.

11. A process for purifying an organic material by removing pyrogenic substances, comprising:
   (a) passing an organic material to be purified over the ultrafilter or the ultrafiltration unit whose removal rate was previously determined and whose integrity was previously validated by the method of claim 1; and
   (b) applying a pressure-hold test to the ultrafilter or the ultrafiltration unit to determine a decrease in pressure, over a predetermined time;

a decrease in pressure comparable to the one previously determined indicating that the removal rate of the ultrafilter or ultrafiltration unit has not changed and that the characteristic pressure for the ultrafilter or the ultrafiltration unit has not changed; thereby preparing a purified organic material from which pyrogenic substances have been removed.

12. The process of claim 11, wherein the decrease in pressure is determined at an ultrafilter which is moistened with a substance selected from the group consisting of water, an aqueous solution, and a mixture of water and an organic solvent.

13. The process of claim 12, wherein an aqueous solution is selected from a group consisting of dilute NaOH, dilute KOH and dilute $NH_3$ solution.

14. The process of claims 11, 12 or 13, wherein the decrease in pressure is determined only after a stabilization time.

15. The process of claims 11, 12 or 13, wherein the measurement of the decrease in pressure is done after ultrafiltration under the same conditions as before the ultrafiltration.

16. The process of claims 11, 12 or 13, wherein the gas used is selected from a group consisting of air, nitrogen, oxygen, hydrogen, and helium.

17. The process of claim 11, wherein the pyrogenic substance is a pathogen.

18. The process of claim 17, wherein the pathogen is a virus.

19. The process of claim 11, further comprising eliminating any pyrogens retained on the ultrafilter or ultrafiltration unit after step (a) by passing a solution capable of dissolving the pyrogens on the ultrafilter or ultrafiltration unit.

20. The process of claim 19, wherein the solution capable of dissolving the pyrogens is an alkaline solution.

* * * * *